(12) United States Patent
Song et al.

(10) Patent No.: US 10,349,892 B2
(45) Date of Patent: Jul. 16, 2019

(54) BIOLOGICAL SIGNAL MEASURING SYSTEM BASED ON DRIVING ENVIRONMENT FOR VEHICLE SEAT

(71) Applicant: HYUNDAI DYMOS INCORPORATED, Seosan-si, Chungcheongnam-do (KR)

(72) Inventors: Hyun Seok Song, Osan-si (KR); Tae Hyoung Yang, Seoul (KR); Woong Jae Lee, Seoul (KR)

(73) Assignee: HYUNDAI DYMOS INCORPORATED (KR)

( * ) Notice: Subject to any disclaimer, the term of this patent is extended or adjusted under 35 U.S.C. 154(b) by 83 days.

(21) Appl. No.: 15/354,889

(22) Filed: Nov. 17, 2016

(65) Prior Publication Data

US 2017/0143270 A1 May 25, 2017

(30) Foreign Application Priority Data

Nov. 24, 2015 (KR) .......................... 10-2015-0164955

(51) Int. Cl.
*A61B 5/00* (2006.01)
*B60N 2/00* (2006.01)
*A61B 5/0205* (2006.01)
*A61B 5/18* (2006.01)

(52) U.S. Cl.
CPC .......... *A61B 5/6893* (2013.01); *A61B 5/0205* (2013.01); *A61B 5/18* (2013.01); *A61B 5/7203* (2013.01); *B60N 2/002* (2013.01); *A61B 2560/0247* (2013.01)

(58) Field of Classification Search
CPC ....... A61B 5/6893; A61B 5/18; A61B 5/0205; A61B 5/7203; A61B 2560/0247; B60N 2/002

See application file for complete search history.

(56) References Cited

U.S. PATENT DOCUMENTS

| | | | |
|---|---|---|---|
| 2003/0136600 A1* | 7/2003 | Breed ...................... | B60J 10/00 180/272 |
| 2014/0293053 A1* | 10/2014 | Chuang ................ | A61B 5/6893 348/148 |
| 2015/0029014 A1* | 1/2015 | Bande Martinez .... | G08B 21/06 340/439 |
| 2016/0267335 A1* | 9/2016 | Hampiholi .............. | G06F 3/013 |
| 2018/0022358 A1* | 1/2018 | Fung .................. | G06K 9/00536 701/36 |

FOREIGN PATENT DOCUMENTS

KR 20150101727 A 9/2015

OTHER PUBLICATIONS

Korean Office Action dated Oct. 11, 2016, Korean Application No. 10-2015-0164955.

* cited by examiner

*Primary Examiner* — Leon Flores (74) *Attorney, Agent, or Firm* — Womble Bond Dickinson (US) LLP (57) ABSTRACT

Provided is a biological signal measuring system based on a driving environment for a vehicle seat. A biological signal measuring device is provided in a seat of a vehicle where most of the body of the driver who is driving a vehicle is consistently located to easily measure a biological signal of the driver and determine and remove noise from the biological signal which is caused by the movement of the driver due to change in a driving environment and a road condition, thereby improving reliability of measurement of a biological signal.

4 Claims, 5 Drawing Sheets

NORMAL CONDITION < THRESHOLD VALUE

THRESHOLD VALUE < SPEED BUMP
SPEED BUMP < THRESHOLD TIME

THRESHOLD TIME < UNPAVED ROAD

BIOLOGICAL SIGNAL MEASURING SYSTEM BASED ON DRIVING ENVIRONMENT FOR VEHICLE SEAT

CROSS-REFERENCE TO RELATED APPLICATIONS

This application claims the priority of Korean Patent Application No. 10-2015-0164955 filed on Nov. 24, 2015, in the Korean Intellectual Property Office, the disclosure of which is incorporated herein by reference.

BACKGROUND

Field

The present disclosure relates to a biological signal measuring system based on a driving environment for a vehicle seat and more particularly, to a biological signal measuring system for a vehicle seat which determines a condition of a driver by removing noise from a signal which is generated due to change in a driving environment and a road condition in a biological signal measuring device located in a vehicle seat, thereby improving reliability of measurement of a biological signal.

Description of the Related Art

Recently, high-tech systems for convenience and safety of a driver are mounted in a vehicle so that the vehicle may be called an assembly of high tech IT technologies. Therefore, the safety and the convenience of the driver are significantly improved so that the purpose of the vehicle surpasses a purpose as a simple transportation means to extend to information, business, and leisure spaces. Therefore, the vehicle is changed as a new level of culture and life means.

Moreover, not only a technology for a safety of the driver, but also a Ubiquitous based medical service, that is, a u-healthcare system is mounted in the vehicle so that the safety and the convenience of the driver are increased and the health management is also enabled while driving the vehicle.

Herein, the u-healthcare system is a health care and medical service which is formed by combining an IT technology and a health and medical service and is available in any places at any time. According to the u-healthcare system, diseases are prevented and remotely managed to maintain and improve health of people.

Recently, the u-healthcare system is grafted onto a vehicle to obtain a biological signal of a driver who is driving the vehicle to analyze health information of the driver. Further, the analysis result is feedbacked to the driver or transmitted to a health management system of the driver.

Further, it is known that the car accident is frequently caused due to an increased degree of fatigue of the driver or sudden change of biorhythm of the driver, in relevance to health condition of the driver. With regard to this, a study to prevent the accident in advance by consistently monitoring the health condition of the driver using a biological signal such as electroencephalogram (EEG), electrocardiogram (ECG), electrooculogram (EOG), skin temperature (SKT), and galvanic skin response (GSR) has been performed.

Therefore, in order to prevent the accident, a method which analyzes a relationship between the biological signal of the driver and the accident to detect sudden change of the biological signal and issue a warning signal to the driver has been used. In this case, a biological signal measuring device mainly detects the biological signal of the driver in a contact manner or a non-contact manner. However, most of the biological signal measuring devices is provided on a steering wheel so that when the driver takes his/her hands off the steering wheel, the biological signal is not detected. Therefore, an input signal in this time is removed as noise. Therefore, it takes a long time to obtain biological information and accuracy of the obtained biological information is lowered.

Further, in the case of a biological signal such as electrocardiogram which is sensitive to external environment change, noise may be caused in accordance with change in a driving environment and movement of the driver. However, a technology which guarantees accuracy and reliability of the biological signal is not currently applied so that reliability of a biological signal analyzing method is not guaranteed correspondingly.

SUMMARY

The present disclosure is directed to providing a biological signal measuring system for a vehicle seat which includes a biological signal measuring device in a vehicle seat on which most of a body of a driver who drives a vehicle is consistently located to easily measure the biological signal of the driver.

Further, the present disclosure is directed to providing a biological signal measuring system based on a driving environment for a vehicle seat which determines and removes noise from a biological signal generated by movement of the driver in accordance with a driving environment and a road condition to improve reliability of measurement of the biological signal.

A biological signal measuring system based on a driving environment for a vehicle seat according to an exemplary embodiment of the present disclosure may include: a biological signal collecting unit which is configured by at least one sensor to sense a biological signal of a driver; a biological signal control unit which receives the biological signal from the biological signal collecting unit to convert and store the biological signal and remove noise from the biological signal; a driving environment collecting unit which transmits driving environment information to the biological signal control unit; and a driver condition determining unit which receives biological signal data which is converted by the biological signal control unit and determines health condition of the driver.

The biological signal control unit may include: a biological signal converting unit which processes the biological signal to convert the biological signal into the biological signal data; a biological signal storing unit which stores the biological signal data; and a biological signal noise removing unit which determines whether noise is included in the biological signal data to remove the noise.

The biological signal noise removing unit may receive the driving environment information from the driving environment collecting unit to determine whether the noise is caused by the driving environment and transmit the biological signal data to the driver condition determining unit according to the noise determining result.

When a measured value of the biological signal is smaller than a threshold value, the biological signal noise removing unit may transmit the biological signal data to the driver condition determining unit without removing the noise, when the time when the measured value of the biological signal is maintained to be equal to or higher than the threshold value is shorter than a threshold time, the biological signal noise removing unit may transmit a biological signal data interval before the noise is generated to the driver condition determining unit, and when the time when the measured value of the biological signal is maintained to be equal to or higher than the threshold value is longer than the threshold time, the biological signal noise removing unit deletes an interval where the noise is generated.

The biological signal measuring system based on a driving environment for a vehicle seat according to the present disclosure configured as described above consistently and easily provides a biological signal of the driver, thereby improving reliability of the biological signal measuring system.

Further, the biological signal measuring system based on a driving environment for a vehicle seat according to the present disclosure configured as described above determines and removes noise from the biological signal which is caused by change in a driving environment and a road condition, thereby improving accuracy and precision of measurement of a sensitive biological signal.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

The present disclosure may have various modifications and several exemplary embodiments to the present invention and specific exemplary embodiments will be illustrated in the drawings and described in detail in detailed description. In describing the present invention, when it is determined that a detailed description of related well-known technology may obscure the gist of the present invention, the detailed description thereof will be omitted.

A general terminology which is currently widely used while considering a function in the present invention is selected as the terminology used in this specification and may depend on the intention of those skilled in the art, or the custom or new technology. However, when a specific terminology is defined to have an arbitrary meaning, the meaning of the terminology may be separately described. Therefore, the terminology used in the specification is analyzed based on a substantial meaning of the terminology and the specification rather than a simple title of the terminology.

The accompanying drawings of the specification are provided so as to easily describe the present invention and shapes illustrated in the drawing may be exaggerated so as to help the understanding of the present invention if necessary so that the present invention is not limited to the drawings.

Hereinafter, preferred embodiments of the present invention will be described in detail with reference to the accompanying drawings.

Figure 1:
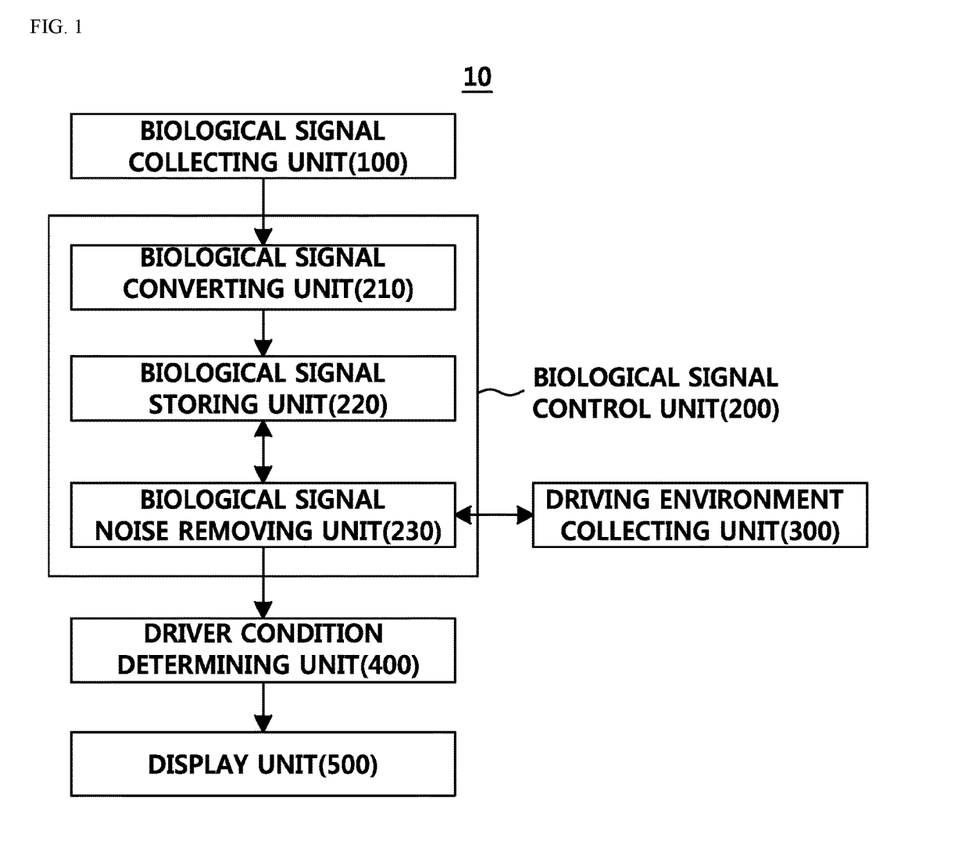
FIG. 1 is a diagram of a configuration of a biological signal measuring system for a vehicle seat according to an exemplary embodiment of the present disclosure.

FIG. 1 is a diagram of a configuration of a biological signal measuring system for a vehicle seat according to an exemplary embodiment of the present disclosure.

As illustrated in the drawing, a biological signal measuring system 10 based on a driving environment for a vehicle seat includes a biological signal collecting unit 100, a biological signal control unit 200, and a driver condition determining unit 400. Herein, the biological signal measuring system 10 may further include a display unit 500.

The biological signal collecting unit 100 is configured by at least one sensor to detect a biological signal of a driver.

The biological signal control unit 200 receives the biological signal from the biological signal collecting unit 100 to convert and store the biological signal and remove noise from the biological signal.

The driving environment collecting unit 300 transmits driving environment information to the biological signal control unit 200.

The driver condition determining unit 400 receives converted biological signal data from the biological signal control unit 200 and determines health condition of the driver.

Figure 3:
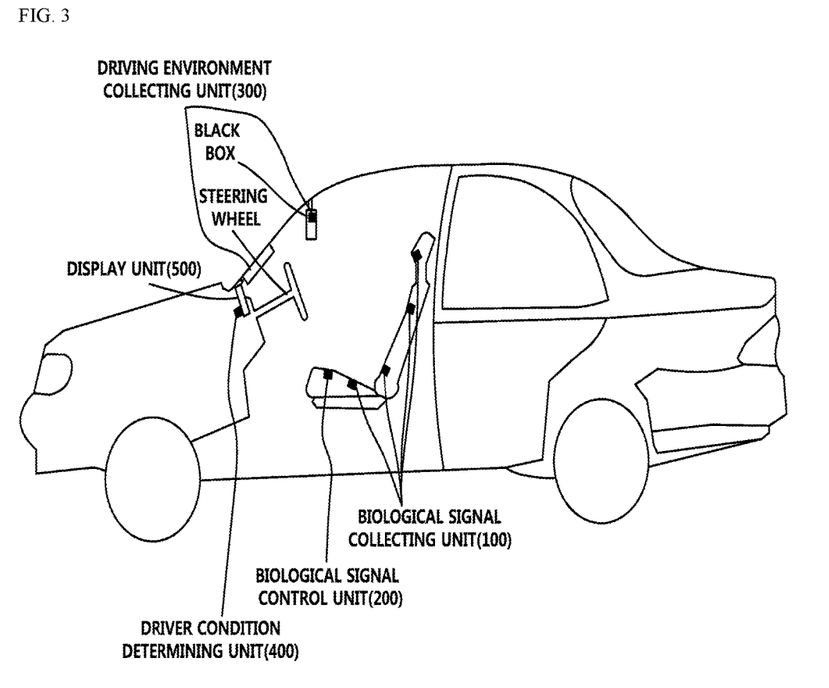
FIG. 3 is a plan view schematically illustrating an internal structure of a vehicle in which a biological signal measuring system for a vehicle seat according to an exemplary embodiment of the present disclosure is provided.
Figure 4:
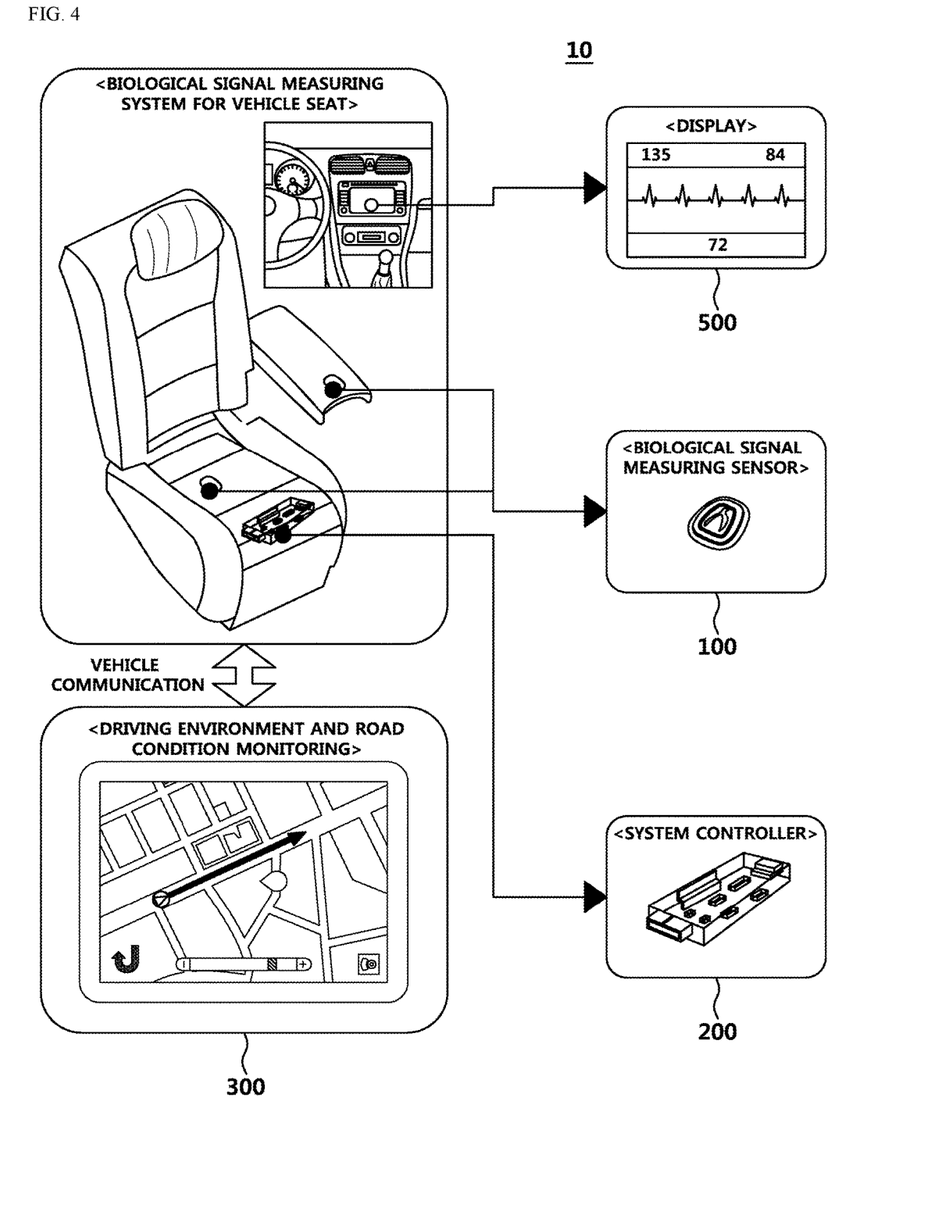
FIG. 4 is an actual image of a biological signal measuring system for a vehicle seat according to an exemplary embodiment of the present disclosure.

FIG. 3 is a plan view schematically illustrating an internal structure of a vehicle in which a biological signal measuring system for a vehicle seat according to an exemplary embodiment of the present disclosure is provided and FIG. 4 is an actual image of the biological signal measuring system for a vehicle seat.

A configuration of the biological signal measuring system for a vehicle seat according to the exemplary embodiment of the present disclosure configured as described above will be described in detail below.

The biological signal collecting unit 100 is provided in the vehicle seat to be fixed thereto. The biological signal collecting unit 100 senses a biological signal of a passenger in a non-contact manner by electrostatic capacitive coupling from minute change in electric field in a free space which is generated by movement of myocardium and a blood vessel of the passenger. The biological signal collecting unit 100 is configured by one or more bio sensors, but the present disclosure is not limited thereto.

Further, the biological signal collecting unit 100 is disposed in an appropriate location where the biological signal of the driver is easily measured, for example, in a back of the vehicle seat which is located near the horizontally same line as a heart. Therefore, the biological signal is measured in real time while the driver is seated on the seat.

Examples of the biological signal include an electrocardiogram (ECG) signal, an electromyogram (EMG) signal, an electroencephalogram (EEG) signal, a galvanic skin resistance (GSR) signal, a blood sugar, a body temperature, a blood pressure, a blood alcohol content, a heart rate, a respiration rate, and a body fat.

The biological signal control unit 200 includes a biological signal converting unit 210 which processes the biological signal to convert the biological signal into biological signal data, a biological signal storing unit 220 which stores the biological signal data, and a biological signal noise removing unit 230 which determines whether noise is included in the biological signal data to remove the noise.

Further, the biological signal control unit 200 is desirably located near the biological signal collecting unit 100 in the seat, but the present disclosure is not limited thereto.

Specifically, the biological signal converting unit 210 may convert an analog electric signal for a biological signal output from the biological signal collecting unit 100 into an amplified digital signal through an A/D converter (not illustrated).

The biological signal storing unit 220 may semipermanently or temporarily store the biological signal data which is converted into a digital signal and may store various programs and various information to drive the biological signal control unit 200.

Therefore, the biological signal storing unit 220 may be provided as a memory such as a hard disk drive (HDD), a solid state drive (SSD), a flash memory, a read-only memory (ROM), and a random access memory (RAM).

The biological signal noise removing unit 230 receives the driving environment information from the driving environment collecting unit 300 to determine whether the noise is caused by the driving environment and transmit the biological signal data to the driver condition determining unit 400 according to the noise determining result.

The driving environment collecting unit 300 may include at least one of a navigation system, a GPS (not illustrated), a camera of a black box, and a front/rear camera (not illustrated) of the vehicle. The driving environment collecting unit 300 collects driving environment information, that is, road condition information such as a speed bump, an unpaved road, a sharp curve, a collision accelerator sensor through the above-mentioned devices and may transmit the information to the biological signal control unit 200 through in-vehicle communication.

As the in-vehicle communication, a near field communication method such as Bluetooth or ZigBee may be used.

The driver condition determining unit 400 determines health condition of the driver using the biological signal data received from the biological signal control unit 200. The health condition of the driver may include a normal condition, an abnormal condition, and an urgent condition. For example, profile information on health condition of the driver may be stored in the driver condition determining unit 400. That is, the driver condition determining unit 400 compares the profile information and the obtained biological signal data to determine the health condition of the driver.

That is, in the profile information, various reference values regarding the normal condition, the abnormal condition, and the urgent condition of the various biological information of the driver may be recorded. The driver condition determining unit 400 compares the biological signal data which is monitored in real time and the reference values to determine whether the health condition of the driver is normal, abnormal, or urgent. For example, according to the profile information, the blood alcohol content may be recorded as that the normal condition is 0.005% or lower, the abnormal condition is between 0.005 and 0.5%, and the urgent condition is 0.5% or higher. When the currently detected blood alcohol content is 0.037%, the driver condition determining unit 400 may determine that the health condition of the driver is abnormal.

The display unit 500 is provided in the vehicle and may output health condition information of the driver which is received from the driver condition determining unit 400. For example, the health condition, a blood pressure, a body temperature, a blood sugar, a blood alcohol content, and the like, may be displayed on a display in the vehicle.

Further, when the health condition of the driver is not normal (that is, the abnormal condition or the urgent condition), the display unit 500 may perform an action according to the health condition. For example, when the health condition is an abnormal condition, a warning message including information on a recommendation for taking a rest or a rest area nearby, or a hospital may be output on the display.

The display unit 500 may be provided as an infortainment device which is provided in the vehicle. For example, the display unit 500 may be a navigation system, a vehicle TV, an A/V system, a black box, a vehicle controlling computer, or the like, which is built in the vehicle.

Further, the display unit 500 may operate not only the display unit 500 but also various devices for convenience in the vehicle according to the condition of the driver. For example, when the driver dozes off at the wheel or the body temperature of the driver is changed, the display unit 500 may operate an air conditioning and heating system and operate a heating system or a massage function of the seat.

Figure 2:
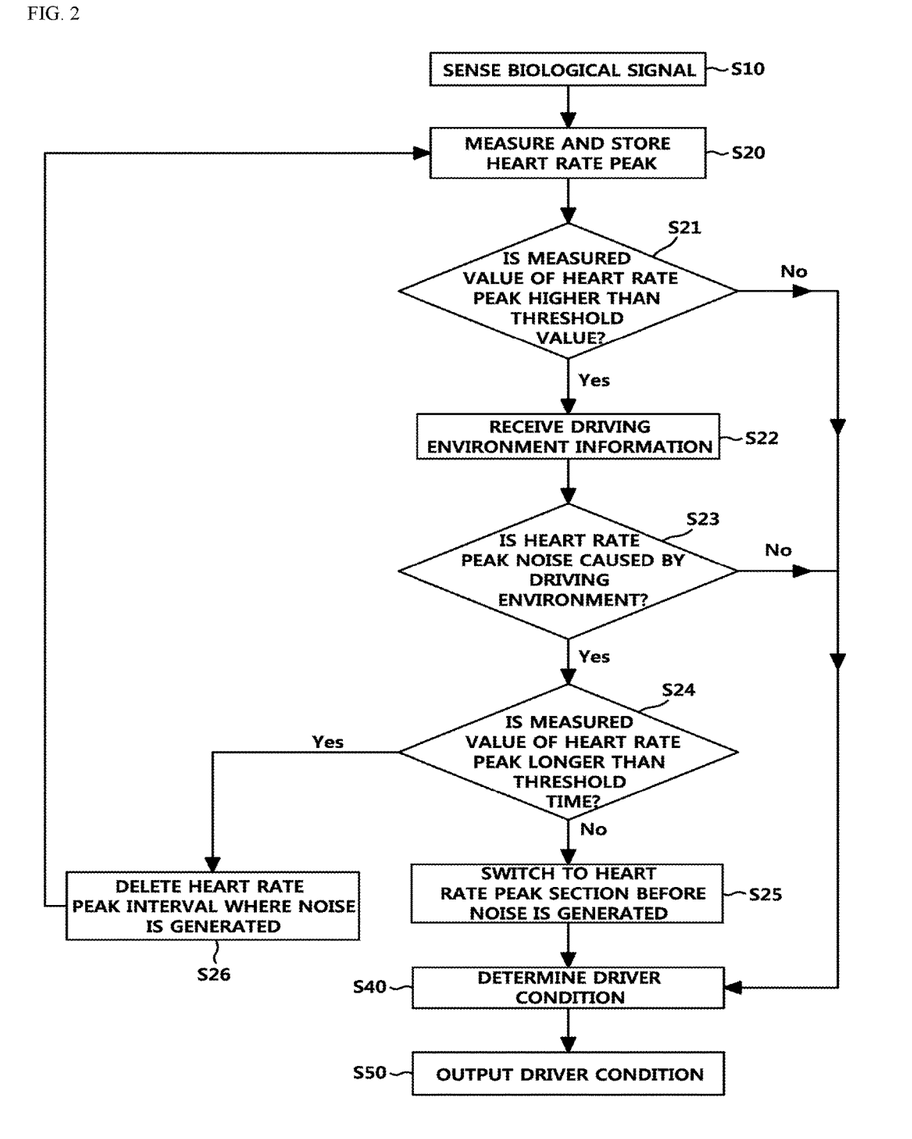
FIG. 2 is a flowchart of biological signal data processing of a driver of a biological signal measuring system for a vehicle seat according to an exemplary embodiment of the present disclosure.
Figure 5:
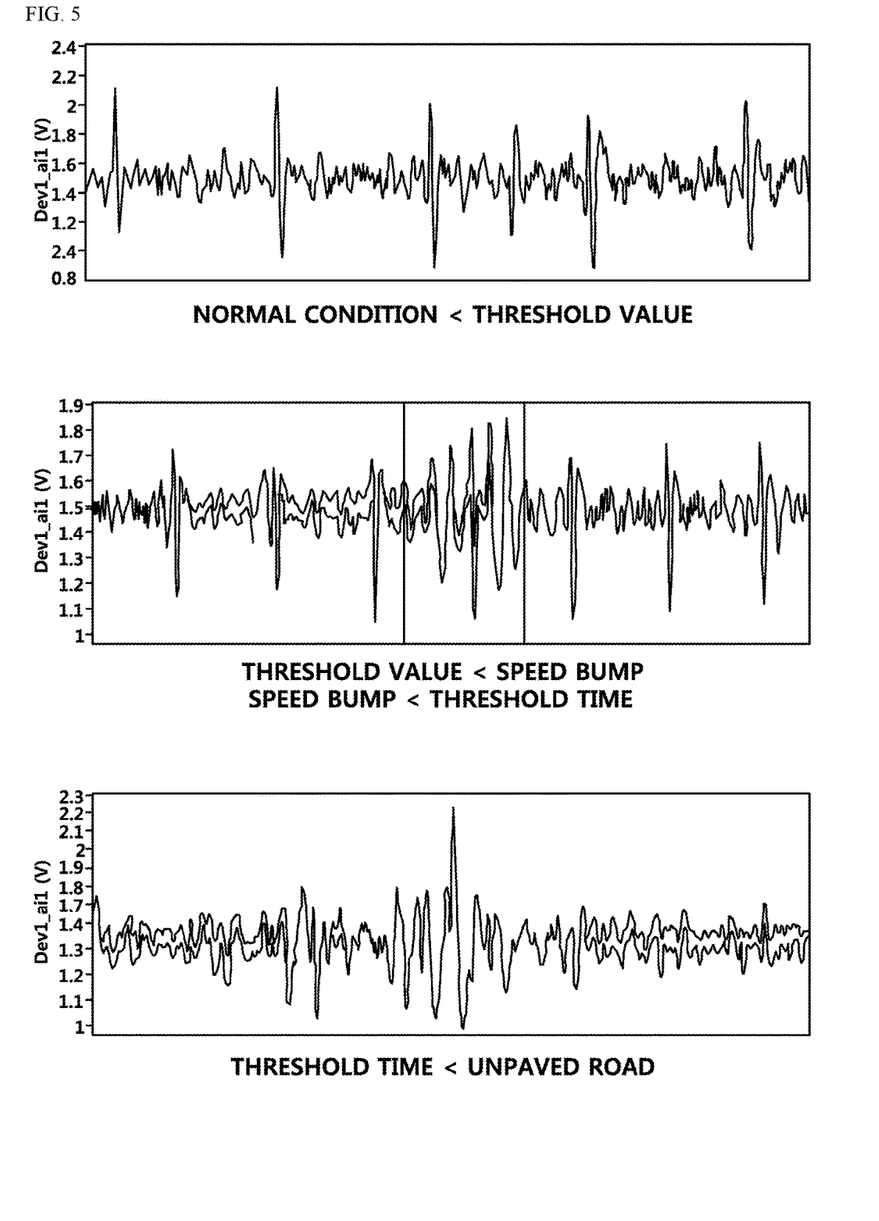
FIG. 5 is a graph of a heart rate depending on whether there is noise measured by a biological signal measuring system for a vehicle seat according to an exemplary embodiment of the present disclosure.

FIG. 2 is a flowchart of biological signal data processing of a driver of a biological signal measuring system for a vehicle seat according to an exemplary embodiment of the present disclosure and FIG. 5 is a graph of a heart rate depending on whether there is noise measured by a biological signal measuring system for a vehicle seat according to an exemplary embodiment of the present disclosure.

An example that the biological signal data is an electrocardiogram signal will be described with reference to FIG. 5. FIG. 5 is an electrocardiogram graph obtained by measuring a heart rate peak using a signal to noise ratio and illustrates different electrocardiograms in accordance with a driving environment.

In the electrocardiogram, various noises such as a noise caused by an external power supply, a noise due to a movement of the driver by the driving environment, or a noise according to electromyogram are generated. Therefore, in order to avoid making a mistake which erroneously calculates the peak of the noise included in the electrocardiogram as a pulse, only the electrocardiogram signal needs to be detected through noise removing algorithm.

When a vibration is generated while driving the vehicle, a posture of the driver may be shifted within a predetermined range from a posture during normal driving. Therefore, a range of a threshold value of the electrocardiogram noise may be determined in consideration of the posture of the driver when the driver leaves the vehicle seat so that the biological signal collecting unit 100 does not normally operate.

For example, when the vehicle is normally driven, force which is applied in a direction which is different from the driving direction of the vehicle is not sensed. However, when the vehicle is driven on the speed bump, the sharp curve, or the unpaved road or a collision is generated, predetermined force which is applied to a direction which is different from the driving direction of the vehicle is sensed. Therefore, when the vehicle is normally driven or force which is applied to the vehicle in a direction other than the driving direction of the vehicle, the biological signal noise removing unit 230 sets a threshold value of an electrocardiogram peak noise. The biological signal noise removing unit 230 determines that the electrocardiogram received from the biological signal storing unit 220 is effective and transmits the electrocardiogram to the driver condition determining unit 400 to determine the health condition of the driver using the same.

Referring to FIG. 2, the biological signal measuring system 10 regularly monitors and collects a heart rate of the driver through the biological signal collecting unit 100 which includes a plurality of bio sensors located in the seat of the vehicle in step S10.

The biological signal control unit 200 converts the heart rate of the driver collected from the biological signal collecting unit 100 into a heart rate peak graph using a signal to noise ratio and stores heart rate peak data which is measured at least for five minutes in the biological signal storing unit 220 in step S20.

Next, the biological signal control unit 200 compares a measured value of the heart rate peak and a threshold value in step S21. When the measured value of the heart rate peak is smaller than the threshold value, the condition may be said to be a stable condition that there is no movement of the driver due to the driving environment. Therefore, the biological signal control unit 200 transmits the heart rate peak data to the driver condition determining unit 400 without removing the measured value of the heart rate peak. In contrast, when the measured value of the heart rate peak is larger than the threshold value, in order to check whether the measured value of the heart rate peak is caused by the driving environment such as a speed bump, an unpaved road, or a sharp curve, the biological signal control unit 200 receives information on the driving environment of the vehicle from the driving environment collecting unit 300 through in-vehicle wireless communication in step S22.

Next, the biological signal control unit 200 checks whether the heart rate peak data is a noise caused by the driving environment. When the heart rate peak noise is not caused by the driving environment, since there is something wrong in the health condition of the driver, the biological signal control unit 200 transmits the heart rate peak data to the driver condition determining unit 400 without removing the noise in step S23.

When the noise of the heart rate peak is a noise which is caused by the driving environment, the biological signal control unit 200 determines whether a time when the measured value of the heart rate peak is maintained to be equal to or higher than the threshold value is equal to or longer than a threshold time in step S24.

When the time when the measured value of the heart rate peak is maintained to be equal to or higher than the threshold value is shorter than the threshold time, the noise may be temporally generated, that is, the vehicle may be driven on the speed bump. Therefore, the biological signal control unit 200 receives a measured value of the heart rate peak before the noise is generated, from the biological signal storing unit 220 to switch a section to remove the heart rate peak noise and transmit the measured value of the heart rate peak to the driver condition determining unit 400 in step S25.

When the time when the measured value of the heart rate peak is maintained to be equal to or higher than the threshold value is longer than the threshold time, the noise is consistently generated because a surface of the road is not smooth as in the case of an unpaved road. Therefore, the biological signal control unit 200 removes all the heart rate peak noise intervals and does not transmit the measured value of the heart rate peak to the driver condition determining unit 400 in step S26. Therefore, the biological signal control unit 200 receives the heart rate peak data when the movement of the driver stops due to the driving environment, that is, the noise of the heart rate peak is reduced, to repeat steps S20 to S24.

The driver condition determining unit 400 determines health condition of the driver with the heart rate peak data received from the biological signal control unit 200 in step S40.

Further, the health condition of the driver which is determined in the driver condition determining unit 400 is output to the display unit 500 which is provided in the vehicle in real time in step S50.

As described above, the biological signal measuring system for a vehicle seat according to the present disclosure consistently and easily provides a biological signal of the driver, thereby improving reliability of the biological signal measuring system.

Further, the biological signal measuring system for a vehicle seat according to the present disclosure configured as described above determines and removes noise from the biological signal which is caused by change in a driving environment and a road condition, thereby improving accuracy and precision of measurement of a sensitive biological signal.

Configurations illustrated in the embodiments and the drawings described in the present specification are only the most preferred embodiment of the present invention and do not represent all of the technical spirit of the present invention, and thus it is to be understood that various modified examples, which may replace the configurations, are possible when filing the present application. The present disclosure is not limited to the specific exemplary embodiment of the present disclosure, and a person of ordinary skill in the art may variously modify and work the present disclosure without departing from the principals of the present disclosure defined in the claims, and the modification belongs to the scope of the claims.

What is claimed is:

1. A biological signal measuring system for a vehicle seat, the system comprising:
   a biological signal collecting unit which is configured by at least one sensor to sense a biological signal of a driver;
   a driving environment collecting unit which is configured by at least one sensor to sense driving environment information;
   a biological signal control unit which receives the biological signal from the biological signal collecting unit and receives the driving environment information from the driving environment collecting unit, and creates a noise determining result based on whether noise in the biological signal is caused by the driving environment, and transmits the biological signal data according to the noise determining result; and
   a driver condition determining unit which receive biological signal data which is converted by the biological signal control unit and determines health condition of the driver,
   wherein when the biological signal data is larger than a threshold value and a direction
   which is different from the driving direction of the vehicle is sensed, the biological signal control unit determines the biological signal is a noise caused by the driving environment,
   wherein when a time when the biological signal is maintained to be equal to or higher than the threshold value is longer than a threshold time, the biological signal control unit does not transmit the biological signal data to the driver condition determining unit.

2. The system according to claim 1, wherein the biological signal control unit comprises:

a biological signal converting unit which processes the biological signal to convert the biological signal into the biological signal data; and a biological signal storing unit which stores the biological signal data; and a biological signal noise removing unit which determines whether noise is included in the biological signal data to remove the noise.

3. The system according to claim 2, wherein the biological signal noise removing unit receives the driving environment information from the driving environment collecting unit to determine whether the noise is caused by the driving environment and transmit the biological signal data to the driver condition determining unit according to the noise determining result.

4. The system according to claim 3, wherein when a measured value of the biological signal is smaller than the threshold value, the biological signal noise removing unit transmits the biological signal data to the driver condition determining unit without removing the noise, when the time when the measured value of the biological signal is maintained to be equal to or higher than the threshold value is shorter than the threshold time, the biological signal noise removing unit transmits a biological signal data interval before the noise is generated to the driver condition determining unit, and when the time when the measured value of the biological signal is maintained to be equal to or higher than the threshold value is longer than the threshold time, the biological signal noise removing unit deletes an interval where the noise is generated.

* * * * *